(12) United States Patent
Kavet et al.

(10) Patent No.: US 6,865,410 B2
(45) Date of Patent: Mar. 8, 2005

(54) APPARATUS AND METHOD FOR MEASURING CURRENT FLOW IN AN ANIMAL OR HUMAN BODY

(75) Inventors: Robert Kavet, San Carlos, CA (US); John C. Niple, San Jose, CA (US); Thomas P. Sullivan, Lenox, MA (US); Luciano E. Zaffanella, Stockbridge, MA (US)

(73) Assignee: Electric Power Research Institute, Inc., Palo Alto, CA (US)

( * ) Notice: Subject to any disclaimer, the term of this patent is extended or adjusted under 35 U.S.C. 154(b) by 154 days.

(21) Appl. No.: 09/920,679

(22) Filed: Aug. 1, 2001

(65) Prior Publication Data

US 2002/0035339 A1 Mar. 21, 2002

Related U.S. Application Data

(60) Provisional application No. 60/223,639, filed on Aug. 4, 2000.

(51) Int. Cl.[7] ............................... A61B 5/05
(52) U.S. Cl. .................. 600/407; 324/692; 600/547
(58) Field of Search ............... 600/547, 372, 600/382, 384, 548, 407, 34, 506, 536; 709/19; 324/691, 692

(56) References Cited

U.S. PATENT DOCUMENTS

| | | | | |
|---|---|---|---|---|
| 4,328,809 A | * | 5/1982 | Hirschowitz et al. | 600/407 |
| 4,557,271 A | * | 12/1985 | Stoller et al. | 600/547 |
| 4,942,880 A | * | 7/1990 | Slovak | 600/547 |
| 5,817,031 A | * | 10/1998 | Masuo et al. | 600/547 |
| 5,897,505 A | * | 4/1999 | Feinberg et al. | 600/547 |
| 5,938,593 A | * | 8/1999 | Ouellette | 600/300 |
| 6,321,112 B1 | * | 11/2001 | Masuo | 600/547 |
| 6,393,317 B1 | * | 5/2002 | Fukuda et al. | 600/547 |
| 2003/0004432 A1 | * | 1/2003 | Assenheimer | 600/547 |

* cited by examiner

Primary Examiner—Eric F. Winakur
Assistant Examiner—Jonathan Foreman
(74) Attorney, Agent, or Firm—Morgan, Lewis & Bockius, LLP

(57) ABSTRACT

An apparatus for measuring contact current includes data acquisition circuitry with at least two sensor contacts to measure the voltage drop across an animal or human body. A portable data processing unit is connected to the data acquisition circuitry to process the voltage data to produce current flow data.

44 Claims, 3 Drawing Sheets

APPARATUS AND METHOD FOR MEASURING CURRENT FLOW IN AN ANIMAL OR HUMAN BODY

This application claims the benefit of Provisional Application No. 60/223,639, filed Aug. 4, 2000.

BRIEF DESCRIPTION OF THE INVENTION

This invention relates generally to measuring and analyzing current flow through an animal or human body. More particularly, this invention relates to a portable contact meter analysis device.

BACKGROUND OF THE INVENTION

For the purposes of this patent, contact current is defined as the current that flows in an animal or human subject when the subject touches (contacts) two different electrically conductive points in the subject's environment. Different conductive points with different voltage potentials cause current to flow in the living body.

Most current measurement systems use one of two basic methods. The first method is to insert a known impedance into the current path and measure the voltage across the known impedance. (Current, voltage, and impedance are all related by Ohm's law, which states that Voltage=Current× Impedance. With two known quantities, one can calculate the unknown quantity, current in this case.) The second method is to attach a coupling transformer around the current path and measure the current via the magnetic field generated from the current flow.

Both methods have significant disadvantages for a contact meter; and at present there are no devices available to measure this contact current. The first method requires that the current path be broken with a fixed impedance and that the fixed impedance not significantly alter the measured current. For contact current, the points of contact can be anywhere on the body. The current flow will generally occur throughout the volume of the body. Contact points can occur at more than two locations with different voltages at each point. Consequently, it is difficult to gather and process this information.

The second measurement method (using a transformer) also has a number of disadvantages. Current transformers of this type are usually insensitive and must be used with large primary currents (Amps). Contact currents are typically small, milliamps (mA) and microamps (uA), and need a sensitive measurement device. Sensitivity can be increased by increasing the size and weight of the transformer, but this makes the devices too cumbersome for human use. Thus, prior art devices have not successfully measured contact current.

An additional problem is that the transformer method measures the magnetic field created by the current. Environments with potential contact currents often have ambient magnetic fields. The transformer measures both the magnetic field from the current flow and the ambient magnetic field, and cannot differentiate the two sources.

Accordingly, it is desirable to provide an improved technique for measuring current flow in an animal or human body.

SUMMARY OF THE INVENTION

An apparatus for measuring contact current includes data acquisition circuitry with at least two sensor contacts to measure the voltage drop across an animal or human body. A portable data processing unit is connected to the data acquisition circuitry to process the voltage data to produce current flow data.

The invention provides a compact, lightweight, low-power device that can be used to flexibly and non-invasively determine the magnitude of current flowing through an animal or human body.

BRIEF DESCRIPTION OF THE DRAWINGS

For a better understanding of the invention, reference should be made to the following detailed description taken in conjunction with the accompanying drawings, in which.

DETAILED DESCRIPTION OF THE INVENTION

Figure 1:
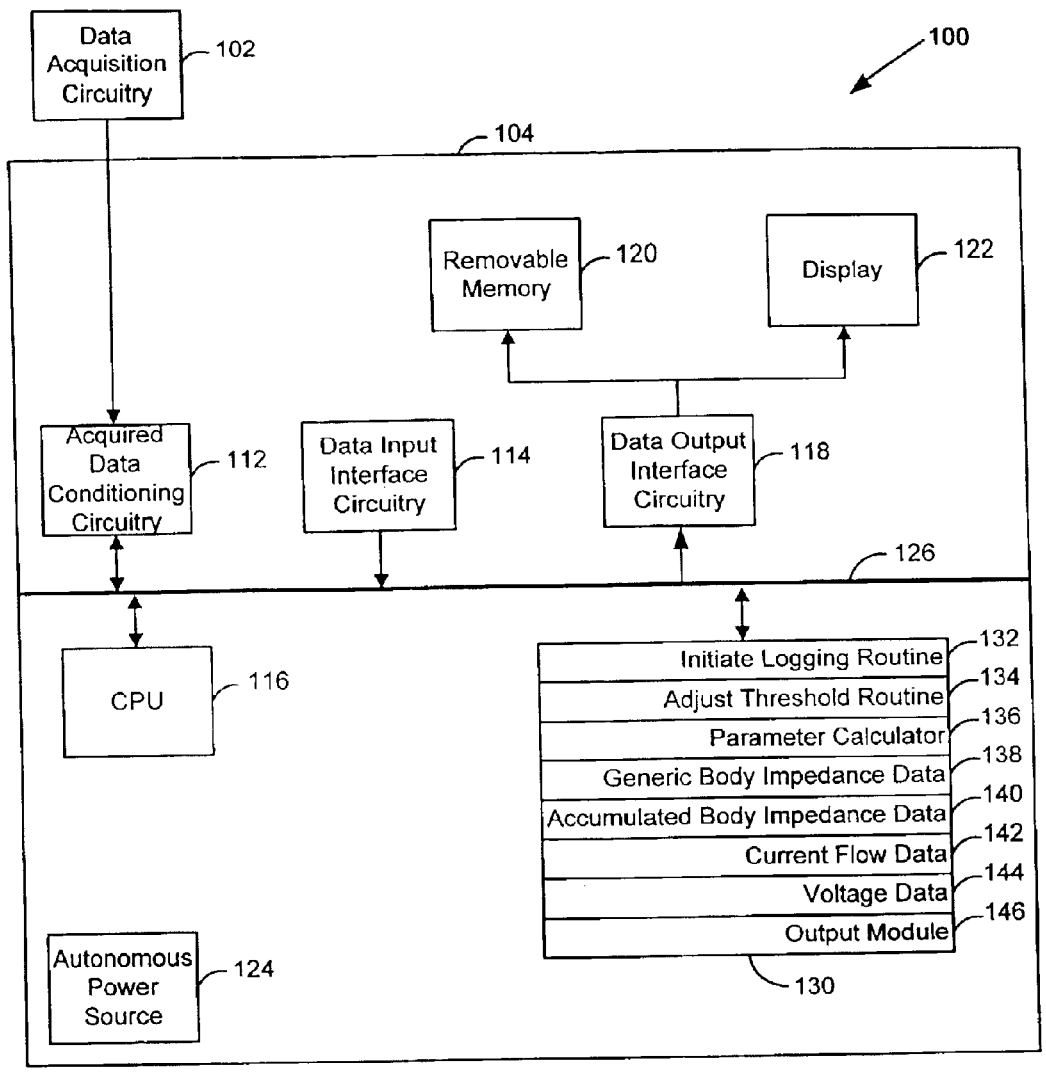
FIG. 1 illustrates a contact meter analysis apparatus in accordance with an embodiment of the invention.

FIG. 1 illustrates a contact meter analysis apparatus 100 constructed in accordance with an embodiment of the invention. The contact meter analysis apparatus 100 includes data acquisition circuitry 102 and a portable data processing unit 104. To make the unit portable, a preferred embodiment of the invention includes an autonomous power source 124. In an embodiment of the invention, the portable data processing unit 104 includes acquired data conditioning circuitry 112 to receive data from the data acquisition circuitry 102. As its name implies, the acquired data conditioning circuitry 112 pre-processes and digitizes the data so that it is in a format useful to the remainder of the circuitry in the portable data processing unit 104.

As indicated in FIG. 1, the acquired data conditioning circuitry 112 and data input interface circuitry 114 apply digital signals to the system bus 126. The data input interface circuitry 114 preferably includes an input mechanism, such as a keypad. A central processing unit (CPU) 116, data output interface circuitry 118, and memory 130 are also connected to the system bus 126. The CPU 116 executes the programs stored in memory 130. The data output interface circuitry 118 receives digital signals from the system bus 126 and is connected to a display 122, preferably an LCD, and a removable memory 120, preferably a compact flash memory. The memory 130 stores a set of executable programs and data, including: an initiate logging routine 132, an adjust threshold routine 134, a parameter calculator 136, generic body impedance data 138, accumulated body impedance data 140, current flow data 142, voltage data 144, and an output module 146. The programs and data stored in memory 130 are described in connection with FIG. 2 and FIG. 3.

Figure 2:
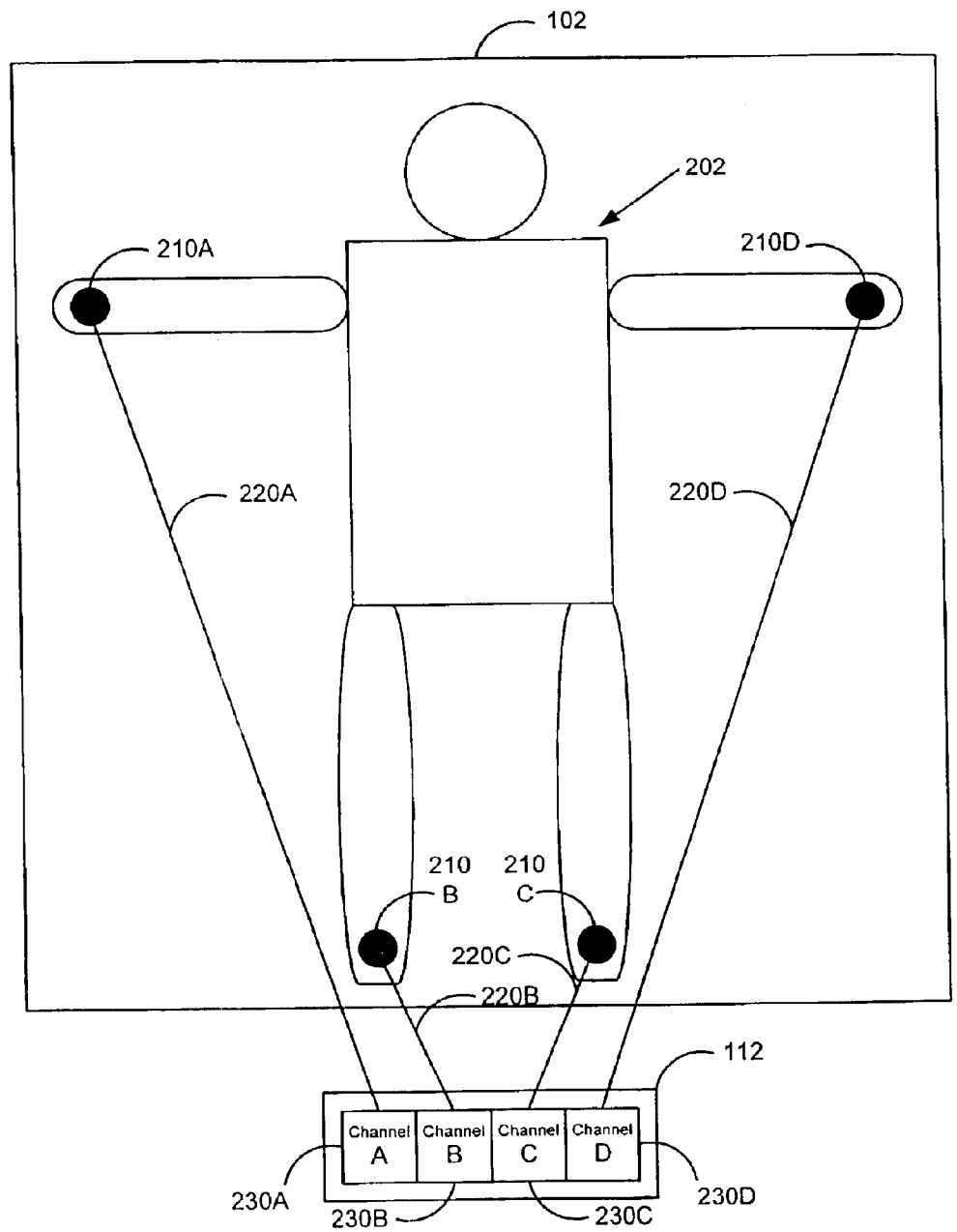
FIG. 2 illustrates the data acquisition circuitry channels in accordance with an embodiment of the invention.

FIG. 2 illustrates an embodiment of the data acquisition circuitry 102 and acquired data conditioning circuitry 112 that utilizes four channels. The electrically conductive skin contacts 210A, 210B, 210C, and 210D, hereinafter referred to collectively as contacts 210, correspond to respective channels of the data acquisition circuitry 102. The contacts 210 are preferably made with skin patches commonly used for medical measurements. The contacts 210 are placed on an animal or human body 202 and are connected via connections 220A, 220B, 220C, and 220D, hereinafter referred to collectively as connections 220, to the conditioning circuitry channels 230A, 230B, 230C, and 230D, hereinafter referred to collectively as channels 230, or individually as a channel 230. The channels 230 make up the acquired data conditioning circuit 112. In one embodiment of the invention, the connections 220 are cables. The invention encompasses both wireless and physical connections.

In general, an overall model of the body's impedance would have high impedance and high variability for the contact areas, skin, and extremities (fingers, hands, feet, toes, head, etc.); and low impedance and low variability for the torso, legs, and arms. In a preferred embodiment of the invention, the contacts 210 are placed on the legs, torso, or arms so that the voltage measured is across the arms, legs, and torso to reduce the impedance variability. Note that in FIG. 2 the contacts 210 are placed on both arms and both legs of living body 202.

Figure 3:
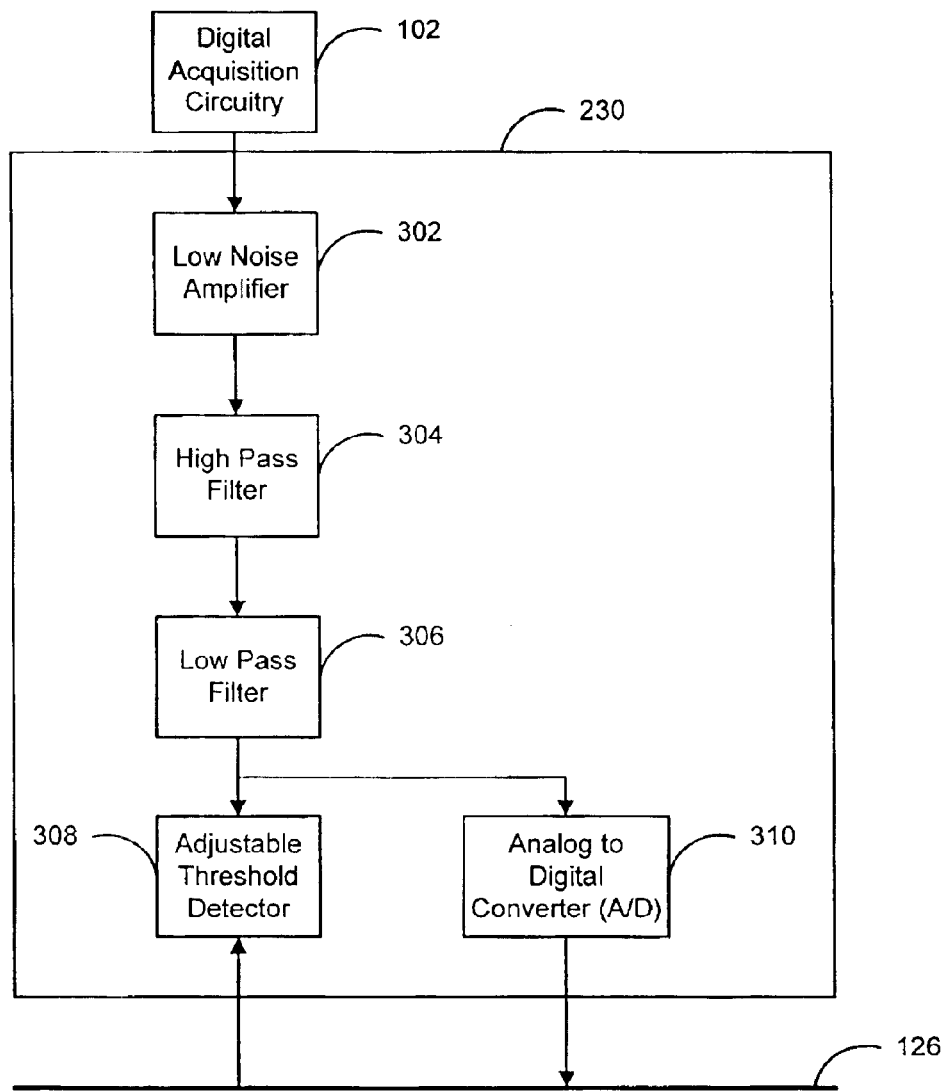
FIG. 3 illustrates a channel of the acquired data conditioning circuitry in accordance with an embodiment of the invention Like reference numerals refer to corresponding parts throughout the drawings.

FIG. 3 illustrates an embodiment of a channel 230 (see FIG. 2). The channel 230 includes a low noise amplifier 302 that buffers the signal and protects the circuitry from outside noise and disturbances. In addition, the low input current (e.g., 10 picoamps (pA)) of the instrument reduces errors from the high impedance contacts 210 (see FIG. 2). The low noise amplifier 302 amplifies the signal. The signal is bandpass filtered through a high pass filter 304 and a low pass filter 306. After the low pass filter 306, the processed signal is fed to an analog to digital converter (A/D) 310 to digitize the signal and to an adjustable threshold detector 308. The adjust threshold routine 134, discussed below, operates to adjust the adjustable threshold detector 308 for each channel 230. The adjustable threshold detector 308 preferably disregards signals between the positive and negative threshold levels at which it is set. The digital output of the analog to digital converter 310, a basic voltage measurement, is applied to the system bus 126 for use by the CPU 116.

In a preferred embodiment of the invention, the output module 146 generates menus that are displayed on display 122. A user selects items on the menu or enters input through the data input interface circuitry 114 to control the behavior of the executable programs stored in memory 130. When so ordered by the user, the output module 146 preferably writes data to the removable memory 120 or to the display 122. In this way, the user can, for example, write current flow data 142 to the removable memory 120 and access that data on a different machine.

In a preferred embodiment of the invention, when the adjust threshold routine 134 is selected, the output module 146 prompts the user through the display 122 for a threshold value for a channel 230. The user may enter threshold values for one or all of the channels 230 through the data input interface circuitry 114. The adjust threshold routine 134 sets the adjustable threshold detector 308 to the threshold values input by the user.

Studies have measured impedances at various locations on the body and the ranges of values and averages for different sized individuals are available. The memory 130 preferably contains generic body impedance data 138 from such studies. Thus, generic body impedance data 138 contains estimated impedances for the living body 202. Preferably, this data includes data for bodies of different heights and weights.

When a user indicates through the data input interface circuitry 114 that the logging is to begin by pressing the appropriate key or sequence of keys, the data input interface circuitry applies a signal to the system bus 126 that the CPU 116 recognizes as an initiate logging command. The CPU 116 then executes the initiate logging routine 132. The initiate logging routine 132 starts logging voltages measured through the data acquisition circuitry 102 and conditioned by the acquired data conditioning circuitry 112. The voltages are stored as voltage data 144 in memory 130. The voltage data 144, as well as the current flow data 142 and accumulated body impedance data 140, could also be processed immediately, without storing to memory 130. In that case, the parameter calculator 136 would be run concurrently with the initiate logging routine 132, rather than subsequently, as discussed below for illustrative purposes.

Utilizing Ohm's Law, current=voltage/impedance, the voltage data 144, and the generic body impedance data 138, the parameter calculator 136 calculates current through an animal or human body 202. Voltage from the voltage data 144 and impedance from the generic body impedance data 138 are available. The results of the calculation are stored as current flow data 142. Note that "known impedances," for the purposes of this calculation, are from the generic body impedance data 138 and are, in the strictest sense, estimates.

The parameter calculator 136 also utilizes Ohm's Law for the purpose of measuring impedance for the living body 202. The user sets current flow data 142 to a known value and runs a current with that known value through the living body 202. Preferably, additional contacts are used for this purpose. Voltage data 144 is accumulated as previously described. The parameter calculator 136 calculates impedance=voltage/current for the current represented in current flow data 142 and the voltage represented in voltage data 144. The calculated impedance is stored in accumulated body impedance data 140.

Utilizing Ohm's Law, current=voltage/impedance, the voltage data 144, and the accumulated body impedance data 140, the parameter calculator 136 calculates current through an animal or human body 202. Voltage from the voltage data 144 and impedance from the accumulated body impedance data 140 are available. The results of the calculation are stored as current flow data 142. Because impedance for each living body 202 is slightly different, calculating known impedances for an animal or human body 202 will generally result in more accurate current flow measurements than using the generic body impedance data 138.

Preferably, the data input interface circuitry 114 includes a button to stop the logging process initiated by the initiate logging routine 132. This button functions as a kill switch or cancel button.

The foregoing description, for purposes of explanation, used specific nomenclature to provide a thorough understanding of the invention. However, it will be apparent to one skilled in the art that the specific details are not required in order to practice the invention. In other instances, well known circuits and devices are shown in block diagram form in order to avoid unnecessary distraction from the underlying invention. Thus, the foregoing descriptions of specific embodiments of the present invention are presented for purposes of illustration and description. They are not intended to be exhaustive or to limit the invention to the precise forms disclosed, obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

What is claimed is:

1. An apparatus for measuring current flow through a living body, comprising:

data acquisition circuitry consisting essentially of a first contact and a second contact configured for placement on a living body to measure voltage between said first contact and said second contact thereby producing voltage data, and a first connector connected at a first end to said first contact and a second connector connected at a first end to said second contact; and a portable data processing unit connected to a second end of said first connector and to a second end of said second connector to process said voltage data and body impedance data to produce current flow data representing an amount of current flow through the living body, wherein said portable data processing unit includes acquired data conditioning circuitry to condition a data signal from said first contact and said second contact.

2. The apparatus of claim 1 further comprising an autonomous power source.

3. The apparatus of claim 1, wherein said acquired data conditioning circuitry includes an amplifier.

4. The apparatus of claim 1 wherein said portable data processing unit includes data input interface circuitry.

5. The apparatus of claim 4 further comprising a keypad connected with said data input interface circuitry.

6. The apparatus of claim 1 wherein said portable data processing unit includes data output interface circuitry.

7. The apparatus of claim 6 further comprising a visual display connected to said data output interface circuitry.

8. The apparatus of claim 6 further comprising a compact removable flash memory card connected to said data output interface circuitry.

9. An apparatus for measuring current flow through a living body, comprising:

data acquisition circuitry consisting essentially of a first contact and a second contact configured for placement on a living body to measure voltage between said first contact and said second contact thereby producing voltage data, and a first connector connected at a first end to said first contact and a second connector connected at a first end to said second contact; and a portable data processing unit connected to a second end of said first connector and to a second end of said second connector to process said voltage data and body impedance data to produce current flow data representing an amount of current flow through the living body, wherein said portable data processing unit includes a central processing unit and a memory storing a set of executable programs and said body impedance data comprised of known body impedances.

10. The apparatus of claim 9 wherein said known body impedances include estimated impedances.

11. The apparatus of claim 9 wherein said known body impedances include calculated impedance measurements.

12. The apparatus of claim 9 wherein said memory stores an output module that controls data storage to a removable flash memory.

13. The apparatus of claim 9 wherein said memory stores an output module that controls the menu of an LCD display.

14. An apparatus for measuring current flow through a living body, comprising:

data acquisition circuitry consisting essentially of a first contact and a second contact configured for placement on a living body to measure voltage between said first contact and said second contact thereby producing voltage data, and a first connector connected at a first end to said first contact and a second connector connected at a first end to said second contact, thereby producing voltage data; and a portable data processing unit connected to a second end of said first connector and to a second end of said second connector to process said voltage data and body impedance data to produce current flow data representing an amount of current flow through the living body, wherein said portable data processing unit includes a central processing unit and a memory storing a set of executable programs and a parameter calculator that compares conditioned data with known body impedances to generate data on said current flow through said living body.

15. The apparatus of claim 14 wherein said memory stores an output module that controls data storage to a removable flash memory.

16. The apparatus of claim 14 wherein said memory stores an output module that controls the menu of an LCD display.

17. An apparatus for measuring current flow through a living body, comprising:

data acquisition circuitry comprising a first contact and a second contact configured to generate voltage data from a living body; and a data processing unit electrically connected to said data acquisition circuitry, wherein said data processing unit comprises a memory configured to store generic body impedance data and an executable program to calculate a current flow through said living body using said voltage data and said generic body impedance data.

18. The apparatus of claim 17 further comprising an autonomous power source.

19. The apparatus of claim 17 wherein said memory stores an output module that controls data storage to a removable flash memory card.

20. The apparatus of claim 17 wherein said memory stores an output module that controls the menu of an LCD display.

21. The apparatus of claim 17, wherein said data processing unit further comprises:

at least two channels electrically connected to said first and second contacts, respectively, wherein each of said channels comprises a low noise filter, a high pass filter, a low pass filter, an adjustable threshold detector and an analog to digital converter;

a system bus electrically connected to said channels;

a central processing unit electrically connected to said system bus; and wherein said memory is electrically connected to said system bus and comprises a set of executable programs.

22. The apparatus of claim 21, further comprising:

an LCD display electrically connected to said data processing unit;

a removable memory capable of being electrically connected to said data processing unit; and an autonomous power supply electrically connected to said data processing unit.

23. The apparatus of claim 17 wherein said data processing unit includes acquired data conditioning circuitry to condition a data signal from said first contact and said second contact.

24. The apparatus of claim 23 wherein said acquired data conditioning circuitry includes an amplifier.

25. The apparatus of claim 17 wherein said data processing unit includes data input interface circuitry.

26. The apparatus of claim 25 further comprising a keypad connected with said data input interface circuitry.

27. The apparatus of claim 17 wherein said data processing unit includes data output interface circuitry.

28. The apparatus of claim 27 further comprising a visual display connected to said data output interface circuitry.

29. The apparatus of claim 27 further comprising a compact removable flash memory card connected to said data output interface circuitry.

30. The apparatus of claim 17 wherein said memory is configured to store generic body impedance data comprising known body impedances.

31. The apparatus of claim 30 wherein said known body impedances include estimated impedances.

32. The apparatus of claim 30 wherein said known body impedances include calculated impedance measurements.

33. A system for measuring current flow through a living body, comprising:

data acquisition circuitry comprising a first contact and a second contact configured to measure a voltage in a living body associated with the living body's environment without applying a current to the living body, thereby providing voltage data;

a data processing unit electrically connected to said data acquisition circuitry, wherein said data processing unit is configured to store said voltage data on a removable memory; and a central processing unit configured to receive said voltage data from said removable memory and to calculate current flow through the living body between said first contact and said second contact from said voltage data and known body impedance data.

34. The system of claim 33 wherein said central processing unit comprises a memory that stores an output module that controls the menu of an LCD display.

35. The system of claim 33 further comprising an autonomous power supply.

36. The system of claim 33 wherein said known body impedance data includes a set of estimated body impedance data.

37. The system of claim 33 wherein said known body impedance data includes a set of calculated body impedance data.

38. The system of claim 33 wherein said data processing unit includes data input interface circuitry, data output interface circuitry and acquired data circuitry to condition a data signal from said first contact and said second contact, wherein said acquired data conditioning circuitry includes an amplifier.

39. The system of claim 38 further comprising:

a keypad connected with said data input interface circuitry;

a visual display connected to said data output interface circuitry; and said removable memory connected to said data output interface circuitry.

40. The system of claim 33 wherein said central processing unit comprises a memory that stores an output module that directs said voltage data to be stored onto said removable memory.

41. The system of claim 40 wherein said removable memory is a compact flash removable memory.

42. The system of claim 40 wherein said voltage data on said removable memory is received by said central processing unit.

43. The system of claim 42 wherein said central processing unit is located within a device that is separate from said data acquisition circuitry.

44. The system of claim 43 wherein said central processing unit processes said voltage data and calculates said current flow through the living body between said first contact and said second contact from said voltage data and said known body impedance data.

* * * * *